United States Patent [19]
Johnson

[11] Patent Number: 4,476,343
[45] Date of Patent: Oct. 9, 1984

[54] OLEFIN OLIGOMERIZATION WITH TANTALUM HALIDE/OXIDE-METAL OXIDE CATALYSTS

[75] Inventor: Thomas H. Johnson, Houston, Tex.

[73] Assignee: Shell Oil Company, Houston, Tex.

[21] Appl. No.: 535,102

[22] Filed: Sep. 23, 1983

[51] Int. Cl.³ .............................................. C07C 2/02
[52] U.S. Cl. .................................................. 585/530
[58] Field of Search ........................................ 585/530

[56] References Cited

U.S. PATENT DOCUMENTS 4,268,706  5/1981  Antos .................................. 208/139
4,430,515  2/1984  Bobsein ............................... 585/530

Primary Examiner—Curtis R. Davis

[57] ABSTRACT

Olefins are oligomerized to higher oligomers by contact with a catalyst comprising a metal oxide substrate having tantalum (V) halide/oxide bound to the surface thereof.

9 Claims, No Drawings

OLEFIN OLIGOMERIZATION WITH TANTALUM HALIDE/OXIDE-METAL OXIDE CATALYSTS

FIELD OF THE INVENTION

This invention relates to a process for oligomerizing olefins to higher oligomers using a catalyst comprising a metal oxide gel having tantalum (V) halide/oxide bound to the surface thereof.

BACKGROUND OF THE INVENTION

Olefin oligomers such as those incompassed by the instant process find use commercially as chemical intermediates. They are, for example, converted to lube oil additives or detergent alcohols. They also find use as gasoline fuel additives for increasing the octane of gasoline.

Conventional processes for preparing these olefin oligomers utilize as catalysts boron trifluoride and aluminum trichloride. Both of these catalyst types have several disadvantages. They are corrosive to the environment in which they operate. Furthermore, they must be continually added to the reaction system, recovered, and returned to the reaction system. This adds some unnecessary cost to the process. The use of a heterogeneous catalyst in a fixed bed process would alleviate the above described problems.

SUMMARY OF THE INVENTION

This invention relates to a process for oligomerizing olefins to higher oligomers utilizing a heterogeneous catalyst. This process oligomerizes olefins, having the following general formula $R^1R^2C=CR^3R^4$ where $R^1$, $R^2$ and $R^3$ are individually hydrogen or alkyl of 1 to about 20 carbon atoms and $R^4$ is alkyl of 1 to about 20 carbon atoms, unless all of $R^1$, $R^2$ and $R^3$ are hydrogen, then $R^4$ is alkyl of 1 to about 6 with the proviso that any two of the Rs may form a divalent alkylene moiety of 2 to about 20 carbon atoms, to higher olefinic oligomers, by contacting the olefins at a temperature of about 10° C. to 350° C. with a catalyst which comprises a metal oxide substrate having tantalum (V) halide/oxide bound to the surface of of the substrate. The catalysts utilized in the instant process are heterogeneous catalysts with the tantalum halide/oxide strongly bound to the metal oxide support. These catalysts experience minimal to insignificant leaching of the tantalum halide into the reactants. Thus, product purity can be maintained at a high level and corrosivity of the reactor and the associated equipment is minimized.

DESCRIPTION OF THE ILLUSTRATIVE EMBODIMENTS

The olefins to be oligomerized in the instant process have the following general formula $R^1R^2C=CR^3R^4$ where $R^1$, $R^2$ and $R^3$ are individually hydrogen or alkyl of 1 to about 20, preferably 1 to about 10 carbon atoms and $R^4$ is alkyl of 1 to about 20, preferably 1 to about 10 carbon atoms, unless all of $R^1$, $R^2$ and $R^3$ are hydrogen, then $R^4$ is alkyl of 1 to about 6, preferably 1 to about 4 carbon atoms with the proviso that 2 of the Rs may form a divalent alkylene moiety of 2 to about 20 carbon atoms. An illustrative, but not exhaustive list of suitable olefins include 1-propene, 1-butylene, 1-pentene, 2-methyl-propene, 2-methyl-1-butene, 2-methyl-2-butene, 2,3-dimethyl-1-butene, 2-methyl-2-pentene, 2-methyl-1-pentene, 2,4,4-trimethyl-2-pentene, 2,4-dimethyl-1-pentene, 2,3,4-trimethyl-2-pentene and similar olefinic compounds. Suitable cyclo-olefinic compounds include 1-methyl-cycloprop-1-ene, 1-methylcyclopent-1-ene, 1,4-dimethyl-cyclopent-1-ene, 1-methyl-cyclohex-1-ene, 1,3,4-trimethyl-cyclohex-1-ene, 1-ethyl-cyclohex-1-ene, 1-propyl-3 methyl-cyclohex-1-ene and related olefinic materials. The oligomerization process is suitably conducted in an inert reaction environment so that the presence of reactive materials such as oxygen is desirably avoided. Reaction conditions are therefore substantially oxygen-free. The precise method of establishing olefin/catalyst contact is not critical. In one modification, the catalyst composition is charged to an autoclave or similar pressure reactor. The olefin feed is introduced, and the reaction mixture is maintained with agitation at a reaction temperature and pressure suitable for the desired reaction. Another modification comprises passing, in a continuous manner, the olefin reactant through a reaction zone in which a supported catalyst composition is maintained. By any modification, the oligomerization process is conducted at moderate temperatures and pressures. Suitable reaction temperatures vary from about 10° C. to about 350° C., but preferably from about 50° C. to about 250° C. The reaction is conducted at or above atmospheric pressure. The precise pressure is not critical, so long as the reaction mixture is maintained substantially in a non-gaseous phase. Typical pressures vary from about atmospheric to about 5000 psig with a range from about atmospheric, preferably from about 100 psig to about 2000 psig being preferred.

Inert solvents may be suitably used in the process of the instant invention. Suitable solvents include for example, the alkanes, such as for example hexane, cyclohexane, heptane, octane, cyclo-octane, and the like.

The products are separated and recovered from the reaction mixture by conventional methods such as fractional distillation, selective extraction, filteration, adsorption, and the like.

During the instant oligomerization process, the starting olefinic reactant material is converted to dimer, trimer, tetramer, pentamer and higher olefins.

The catalysts utilized in the process of the instant invention comprise pentavalent tantalum (also written as tantalum (V)), halogen (or halide), oxygen (or oxide) and a solid metal oxide substrate wherein at least one valence of tantalum is bound to oxygen, which oxygen is bound to the substrate, at least one valence of the tantalum is bound to halogen and the remaining tantalum valences are bound to halogen and/or oxygen, which oxygen may or may not be bound to the substrate. The halogens are fluorine, chlorine, bromine, iodine and mixtures thereof. Preferred halogens are fluorine and chlorine.

The metal oxide-tantalum (V) halide/oxide compositions used in the process of the instant invention are preferably prepared by a process comprising reacting under anhydrous conditions a suitable metal oxide substrate which has water chemically bound as hydroxyl and which is substantially free from absorbed water with tantalum pentahalide vapor and thereafter recovering the product. Thus, are produced metal oxide compositions having tantalum (V) halide/oxide bound to the surface thereof. By the term "bound" it is meant herein that the pentavalent tantalum has at least one valence bound to an oxygen which is part of the metal oxide substrate. By the term "surface" it is meant both the external and internal pore surfaces which are accessible to the tantalum pentahalide vapor during the preparation process.

The catalytic compositions utilized in the instant process basically comprise metal oxide substrates having tantalum (V) halides/oxides reactively bound to the surface of said substrate. The halides are selected from the group consisting of fluoride, chloride, bromide, iodide and mixtures thereof. Preferred halides are fluoride and chloride. The compositions are generally prepared by a process which comprises contacting a hydroxyl-containing metal oxide in a substantially anhydrous state with tantalum pentahalide in the vapor state and allowing the vapor to react with the substrate in an atmosphere which is substantially oxygen- and water-free. In the preferred process, sublimation of the tantalum pentahalide is used to put the tantalum pentahalide in the vapor state. Tantalum pentachloride is the preferred sublimation agent, producing the highest metal leadings on the metal oxide substrate. The use of tantalum pentabromides, iodides or fluorides as sublimation agents produces compositions having metal loadings of less than one percent.

A variation of the above process is utilized to produce a composition containing mixed halides, particularly mixed chlorides and fluorides. In this variation a tantalum (V) chloride/oxide-metal oxide composition is first prepared by reactive sublimation. The tantalum (V) chloride/oxide-metal oxide composition is then contacted with an oxygen-containing gas or a chemical compound containing oxygen which is weakly covalently bonded to the compound. It is postulated that oxygen replaces part of the halide of the composition. The material is then reacted with a liquid or gaseous fluorinated hydrocarbon which is believed to react preferentially with the oxygen bound only to the tantalum, producing, it is postulated, a composition containing various mixtures of chlorides, fluorides, oxides, oxychlorides, oxyfluorides, oxychlorofluorides, etc., depending on reaction conditions. Analyses of compositions prepared in this fashion shown that they contain varying amounts of chlorine and fluorine along with amounts of oxygen (not bound to the substrate) ranging from insignificant to moderate, depending on the degree of fluorination obtained using the fluorinated hydrocarbon. The amount of oxygen remaining can be varied by choice of fluorinated hydrocarbon and reaction conditions. Reaction temperatures and pressures are not critical. Temperatures of room temperature or greater are generally suitable. Different fluorinated hydrocarbons will have different optimum temperatures, pressures and times of contact, and these can readily be determined by routine experimentation. Particularly, suitable fluorinated hydrocarbons are the Freons, such as, for example, Freon 12 ($CF_2Cl_2$), Freon 14 ($CF_4$), Freon 23 ($CHF_3$), Freon 112 ($CCl_2F-CCl_2F$), Freon 116 ($CF_3-CF_3$), Freon 142 (chlordifluor-methyl methane), Freon Cl38 (octafluorocyclobutane) and similar materials. One particular advantage of this process is that it allows the preparation of compositions containing higher amounts of fluoride then does the process using reactive sublimation of tantalum pentafluoride alone. Compositions containing the fluoride are more resistant to oxygen degradation than the compositions containing chloride along. Thus, when the mixed chloride/fluoride compositions are used as catalysts, the feeds need not be purged of oxygen and air is no longer a poison. Feeds containing oxygen (e.g., $O_2$, peroxide, etc.) however, will still compete for catalyst sites and, hence the observed rates of reaction can be reduced.

As noted above, a modification of the basic catalyst composition utilized in the process of the instant invention can be obtained by contacting the tantalum (V) halide/oxide-metal oxide compositions with oxygen or a compound containing oxygen which is weakly covalently bonded to said compound. Illustrative of said compounds are the peroxides and peroxy compounds, both organic and inorganic, the hypohalide's etc. It is postulated that contact of the instant compositions with oxygen or the indicated oxygen-containing compounds converts part of the halogen on the composition to oxygen which is not bound to the substrate. Thus, there are two possible types of oxygen bound to the pentavalent tantalum of the composition. One type is the oxygen(s) which is bound to the tantalum and to the substate. This presence of this type of oxygen is required to produce the catalyst compositions. The other type of oxygen which optionally may be present is oxygen bound only to the tantalum of the composition. Thus, at least one valence of pentavalent tantalum is bound to oxygen which is bound to the substrate, at least one valence of the tantalum is bound to halogen and the remaining tantalum valences are bound to halogen and/or oxygen which is or is not bound to the substrate. This modification containing the optional oxygen may be effected either inadvertently or purposefully. It may be effected by contact with oxygen or oxygen-containing compounds present as additives or impurities in feed streams when the compositions are used as catalysts. For many reactions the instant compositions provide for very active catalysts. When these very active catalysts are used in packed-bed flow reactors, they can lead to hot spots and reactor runaway. The activity of the catalyst can be moderated by contact with oxygen or oxygen-containing compounds as described above.

Tantalum (V) halides readily sublime and thus lends themselves to a preferred method of preparation which is called "reactive sublimation" wherein tantalum pentahalide(s) is sublimed into an anhydrous, non-oxidizing atmosphere and allowed to contact and thus react with the hydrogen-containing metal oxide substrate. In the preparation of these compositions by reactive sublimation, it is important that the reaction be carried out under substantially anhydrous conditions and in a neutral or reducing enviroment to prevent decomposition of the tantalum chloride.

In this preferred method of preparation the tantalum (V) halide is sublimed by suitable application of temperature and/or vacuum into an essentially anhydrous and oxygen-free atmosphere where it is allowed to contact and react with a substantially anhydrous metal oxide substrate. Any temperature and/or vacuum which causes the tantalum pentahalide to sublime is suitable. Temperature to about 200° C. are suitable. Frequently the metal oxide substrate is heated during reaction, say up to about 200° C. This heating is not critical to the preparation of the catalyst, but is has been found that by so heating, a more even distribution of the tantalum halide on the metal oxide substrate is effected. After reaction, the metal oxide composition is frequently subjected to an additional period of time at sublimation conditions without the presence of a tantalum pentahalide source. This extra step allows for any unreacted tantalum pentahalide to be a sublimed off of the metal oxide composition. The metal oxide substrate before use is frequently subjected to a heat treatment to remove absorbed water. Vacuum can also be applied. Generally, if this pretreatment temperature is too low, free water will remain and if the temperature is too high, sintering of the metal oxide substrate will occur, both of which will adversely affect the catalytic properties of the composition. Generally, the most desirable pretreatment temperatures of the metal oxide substrate range from about 200° to 400° C.

It is postulated that when tantalum pentahalide reacts with the hydroxyl group of a metal oxide substrate, that the reaction may be illustrated variously as follows (using chloride as an illustrative halide):

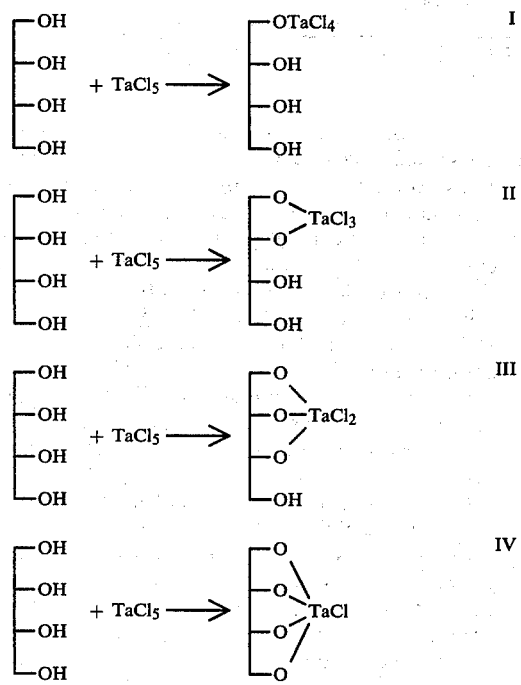

In the final composition a mixture of the above described reaction products will exist. The distribution of the products is believed to be affected by reaction conditions, such as temperature. When tantalum pentahalide is used to prepare the compositions, analysis of chlorine/tantalum ratios in compositions containing about 8–17% w tantalum has shown Cl/Ta atomic ratios ranging from about 2.5:1 to about 3.5:1.

Thus, depending on the tantalum halide content desired in the final composition, a tantalum pentachloride vapor is reacted with metal oxide substrate until a part or the whole of the hydroxyl group population of the gel is exhausted.

The reaction between the tantalum pentahalide vapor and the metal oxide substrate is carried out at temperatures ranging at room temperature to elevated temperatures, say 150° to 200° C. or higher. The reaction is normally carried out in an anhydrous, i.e., free from water vapor, atmosphere. The atmosphere should further be a neutral or reducing atmosphere, i.e., oxygen-free. Dispersal of tantalum pentachloride vapor in a vacuum provides a quite suitable atmosphere for reaction with the metal oxide gel.

The metal oxide-tantalum (V) halide/oxide compositions used in the instant invention may be produced in virtually any physical form, as for example, they may be pellets, beads, extrudates, microspheres and in other particular forms, as for example rings, saddles and the like, and in porous or non-porous form.

The metal oxides that are useful as substrates to prepare the catalysts used in the instant process are those inorganic oxides which have hydroxyl groups attached to the surface of the substrate. The hydroxyl groups provide the means by which the tantalum (V) pentahalides are bound to the surface of the substrate. Any metal oxide which has surface hydroxyl (or oxyhydroxyl) groups can be utilized as a substrate.

The term "metal oxide" although used herein in the singular tense, is meant to include the single oxides such as silica, or alumina as well as plural and complex oxides such as silica-alumina, silica-aluminathoria, zeolites and clays.

The preferred metal oxide substrates are the porous solid inorganic oxides which are conventionally used as cataysts and catalyst supports. Non-limiting examples of these types of materials include those having a major component of silica or alumina or both, such as, example, alumina and aluminous materials; silica and siliceous materials; clays, particularly open lattice days; and crystalline aluminosilicates (zeolites). Non-limiting examples of aluminous and siliceous materials include, for example, silica-alumina, silica-magnesia, silica-zirconia, silica-titania, alumina-chromia, alumina-ferric oxide, alumina-titania as well as ternary compositions such as, for example, silica-alumina-thoria, silica-alumina-zirconia, etc. Non-limiting examples of crystalline aluminosilicates useful as substrates include synthetic zeolites, such as, for example, A, X, Y, L and ZSM types such as ZSM-5 and others and naturally occurring zeolites, such as eriorite, faujasite, mordenite, sodalite, cancrinite and others. Non-limiting examples of open lattice clays useful as substrates include bentonite, montmorillonite and others. In a preferred embodiment, the metal oxide should have a major component of silica or aluminum or a mixture of both.

Particularly suitable as substrates are those solid inorganic oxide compositions known as metal oxide gels or gel oxides.

The gel oxides which are particularly suitable for use in preparing the catalytic compositions used in the process of the instant invention are any of the metal oxide gels that are well known in the catalytic art useful as either catalyst base materials or as promoting materials in catalyst compositions. Additionally, the term "metal oxide gel" and "gel oxide" as used herein shall also include the plural oxide gels, i.e., those that contain mixtures of compounds of two or more metal oxides. A metal oxide gel is basically a metal oxide that contains chemically bound water in the form of hydroxyl groups or oxyhydroxyl groups as opposed to absorbed water and water of hydration, although absorbed water and water of hydration may also be present. They are typically prepared by the precipitation of the metal component(s) in an aqueous medium. Upon calcination at sufficiently elevated temperatures, water is given off and the gel is converted to the oxide with two hydroxyl moieties giving one molecule of water and an oxygen is attached to a metal ion. Illustrative of gel oxide base materials used to prepare the composition of this invention are aluminas, silicas, alumina-silicas, alumina-zirconias, silica-zirconias and the like, including naturally occurring hydrous oxide minerals such as clays such as, for example, the kaolinites, the the montmorillonites and the like. Among the clays the open lattice clays are particularly desirable. Also inclined are the zeolites, both natural and synthetic. The structure of the gel oxides can range from amorphous to highly crystalline. Preferred oxide gel materials are selected from the group consisting of alumina, silica, alumina-silica, crystalline aluminosilicates (zeolites) and open lattice clays.

Since the tantalum (V) halide is bound to the surface of the metal oxide by a reaction of the halide with the metal oxide substrate, the metal oxide must have, before reaction, pendant surface hydroxyl groups attached to the surface. After reaction the metal oxide may or may not have surface hydroxyl groups, depending on the degree of reaction with the tantalum (V) halide.

Prior to use the metal oxide substrate should be substantially free of absorbed water, i.e., "substantially dehydrated or anhydrous". The absorbed or free water is removed by heating the substrate at temperatures ranging from about 100° C. to about 900° C. prior to contact with the tantalum pentachloride vapor. Any environment that provides for drying is suitable such as air, vacuum, inert gas such as nitrogen, etc. The dried substrate should be kept away from a humid atmosphere after drying. It is understood that a dried metal oxide substrate prior to use in preparing the catalysts will still contain chemically bound water in the form of hydroxide and oxyhydroxide.

An aluminum oxide gel is one of the preferred substrates. This alumina can be any of the variety of available aluminas. These are commercially available under various names such as alumina gels, activated aluminas, gamma aluminas, etc. Regarding purity of the alumina, it may be stated that small amounts of impurities are not generally detrimental, and may be beneficial when the impurity is present as a cogel. In fact "impurities" may be purposely added for catalytic effects. The following table lists several commercial aluminas and their properties which are found suitable.

| Alumina | Surface Area, m$^2$g | Pore Vol. cc/gm | Na, ppm | SO$_4$,= % wt | Fe$_2$O$_3$ % wt | Cl,− % wt |
|---|---|---|---|---|---|---|
| CCI[a] | 252 | 0.8 | 160 | 0.06 | — | 0.02 |
| KA-209[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |
| Norton | 218 | 0.62 | 51 | 0.03 | — | 0.03 |

[a]Catalysts & Chemicals, Inc., now United Catalysts
[b]Kaiser
[c]Reynolds Corp.
[d]American CyanamidCorp.
[e]Conoco Corp.
[f]Filtrol Corp.

Silica gel is also another preferred substrate. These are readily available commercially and are essentially substantially dehydrated amorphous silica. These materials are available in various density grades, from low density with surface areas ranging from about 100–300 m$^2$/g to regular density with surface areas up to about 800 m$^2$/g. The commercially available materials are used as dessicants, selective absorbents, catalysts and catalyst supports. Regarding purity of the silica, it may be stated that small amounts of impurities are not generally detrimental and may be beneficial when the impurity is present as a co-gel. In fact, "impurities" may be purposely added for catalytic effects. The following table lists several commercial silicas and their properties which are found suitable.

| Support | Surface Area, m$^2$/g | Pore Vol, cc/g | Density g/cc | Particle Size |
|---|---|---|---|---|
| Davison* Grade | 952 SiO$_2$ | 300 | 1.65 | 0.35 | 70 mesh (avg) |
| Davison Grade | 59 SiO$_2$ | 300 | 1.15 | 0.38 | 8 mesh |
| Davison Grade | 57 SiO$_2$ | 300 | 1.0 | 0.4 | 100 mesh |
| Davison Grade | 12 SiO$_2$ | 700 | 0.54 | 0.75 | 20 mesh |
| Davison Grade | 03 SiO$_2$ | 750 | 0.43 | 0.7 | 8 mesh (avg) |

*Manufactured by Davison Chemical Div., W. R. Grace & Co.

Other preferred substrates are the aluminosilicates. These materials contain various mixtures of aluminum and silicon oxides. They are readily available commercially and are generally employed as cracking catalysts. Typically they contain from about 50 to about 95, preferably from about 70 to about 90 percent by weight of silica. Illustrations of commerically available aluminasilicas are Davison Grade 980-25 (manufactured by Davison Chemical Division, W. R. Grace & Co.) which contains about 75% SiO$_2$ and 25% Al$_2$O$_3$ and Davison Grade 980-13 which contains about 87% SiO$_2$ and 13% Al$_2$O$_3$. These materials can be prepared in a conventional fashion, as for example by co-precipitation, cogellation, or by spray drying.

Encompassed within the term "aluminosilicates" are most of the zeolites. The zeolites are found to be specifically useful as substrates. Zeolites are ordered, porous crystalline aluminosilicates having a definite crystalline structure within which there are a large number of small cavities which are interconnected by a number of still smaller channels. Zeolites useful as substrates may be either synthetic or natural. At least 34 species of zeolite minerals are known and the synthetic zeolites number in the hundreds. Any zeolite will be useful as a substrate provided that the zeolite, prior to reaction with tantalum pentahalide, contains chemically bound water in the form of hydroxyl groups. Depending on the state of reaction, the reacted product may contain no hydroxyl groups if all such groups were reacted with the tantalum pentahalide, or there may be unreacted hydroxyl groups still present.

Further descriptions of the preparation of the catalysts used in the instant process are found in application Ser. No. 527,535, filed Aug. 29, 1983, incorporated by reference herein.

The tantalum pentahalides utilized to prepare the compositions used in the process of the instant invention are readily obtainable commercially.

The compositions utilized as catalysts in the instant invention are used in typical fashion, for example, in packed beds or in fluidized beds. In operation, a process stream containing the olefin to be oligomerized, optionally in combination with an inert solvent is passed over a catalyst bed at a temperature ranging from about 10° C. to about 250° C., and a pressure preferably ranging from about atmospheric to about 5000 psig.

Upon completion of the reaction, the product obtained can be separated into its individual components of product, by-product and reactant by simple means, such as for example, by distillation.

The catalysts described herein, when utilized in the process of the instant invention provide distinct advantages over the use of unsupported materials such as tantalum pentachloride. The catalysts are heterogeneous and can readily be separated from reaction products. The described catalysts are very resistant to leaching, thus, minimizing product contamination and further minimizing corrosion of plant equipment.

The instant process thus comprises an improved process for oligomerizing olefins with a catalyst composition comprising a metal oxide substrate having tantalum (V) halide/oxide bound to the surface of the substrate. The process of the instant invention and the preparation of the compositions used as catalysts in the instant invention will be further described below by the following illustrative embodiments which are provided for illustration and are not to be construed as limiting the invention.

ILLUSTRATIVE EMBODIMENTS

Catalyst Preparation

A. The following illustrates the preparation of a catalyst composition which is utilized in the instant invention. A 200-ml Schlenk flask containing 50–75 g of silica gel (Davison 57, −60+100 mesh) was heated to 300° C. under a vacuum of ca. 0.1 torr for 16–20 h. The flask was moved into a dry box whereupon 6.5 g of the silica was placed on one side of a fritted Schlenk tube. Tantalum chloride (6.0 g) was placed on the other side of the frit. The $TaCl_5$ end of the tube was wrapped with heating tape and then an insulation wrap was installed along with a Thermocouple wire. A vacuum of ca. 0.1 torr was applied at the end of the silica-containing section. The deposition was carried out overnight (16–20 h) at 150° C. with the tube mounted horizontally. The siliceous material was removed in a dry box and then subjected to a vertical sublimation in order to remove any condensed but unreacted $TaCl_5$.

B. The following technique is been found to result in a somewhat more homogeneous catalyst then the above described technique and is utilized where uniformity is important. In this preparative technique a glass scrubbing bottle was modified by internally adding a coarse fritted disc which divided the bottom into an upper section and a lower section. The lower section was fitted with a stoppered connection which allowed it to be charged with tantalum pentachloride and the upper section was fitted with a vacuum stopcock connection which allowed it to be closed off or to be connected to a vacuum. To the modified gas-scrubbing bottle were added about 20 g of $TaCl_5$ to the bottom section and about 60 g of Davison 57 silica (−20+30 mesh, pretreated at 300° C. under 0.1 torr vacuum for 12–24 h) to the top section. Both sections were loaded in a dry box containing a nitrogen atmosphere. The bottom section was stoppered and the top section had the vacuum stopcock closed before removing from the dry box. The bottom section of the bottle was immersed into an oil bath and heated at about 150° C. The top section was wrapped with heating tape and heated to about 150° C. A vacuum (ca 0.1 torr) was applied at the top of the bottle. The heating and vacuum phase of the preparation was simultaneous and carried out over a period of 18 h. At the end of 18 h, the bottle (vacuum stopcock closed) was put back into the dry box and 20 g a fresh $TaCl_5$ was added to the bottom section. The rest of the procedure was then repeated for another 18 h. Then the silica was removed, in a nitrogen-filled dry box, and vertically sublimed at 150° C. and 0.1 torr for 18 h. This step was employed to remove any deposited but unreacted $TaCl_5$ on the silica surface. A small (<200 mg) of $TaCl_5$ was generally collected on the cold finger of the sublimator.

C. In a variation of the process just described above 24 milliliters of the tantalum (V) chloride-silica composition was added directly to a flow reactor and then subjected to an air flow at 200° C., 100 psi at a GSHV of 10,000 $h^{-1}$ for 30 minutes. Then, $CF_4$ (Freon 14) was passed through the bed at 200° C., 100 psi and a GHSV of 240 $h^{-1}$ for a period of 2 hours. Analysis of the resultant composition of the instant invention by neutron activation showed it to contain about 15.7% w Ta, 3.6% Cl and 0.40% w F.

D. In another variation of the just described process, 12 milliliters of the tantalum (V) chloride-silica composition was added to a fixed-bed flow reactor and treated with air at a flow rate of 4 l/min for 15 minutes at 100 psi and 200° C. The air-treated material was then treated with Freon 12 ($CF_2Cl_2$) at 200° C. and 70 psi at a flow rate of 2.4 l/hr for 5 hours. The flow tube was then sealed and left under an atmosphere of Freon 12 at 200° C., 75 psi for 60 hours. Analysis of the resultant composition of the instant invention by neutron activation showed it to contain about 17.5% w Ta, 1.9% w Cl and 5.7% w F.

Process

To a fixed-bed, vertical flow reactor were charged 4.8 grams of catalyst prepared as described above. The catalyst contained 12.9% w tantalum. Isobutylene was fed to the reactor at a rate of 1.8 g/min (WHSV of 22 $hr^{-1}$). The reactor was operated at a temperature of 50° C. or 100° C. in an upflow or downflow mode. After two residence times samples were obtained and analyzed. The results are shown in Table I.

The above process was repeated in a similar fashion with 1-butene and propylene as feedstocks. The reaction conditions and results are shown in Table I.

TABLE I

OLIGOMERIZATION OF BUTYLENES

| Olefin | Flow Direction | Catalyst Prep. Proc. | Temp., °C. | Press., PSI | WHSV, $H^{-1}$ | Conversion (%) | Selectivity $C_8^=$ (%) | $C_{12}^=$ (%) | $C_{16}^=$ (%) | $C_{20}^=$+(%) |
|---|---|---|---|---|---|---|---|---|---|---|
| Isobutylene | Upflow | A | 50 | 500 | 22 | 85 | 14 | 61 | 19 | 6 |
| Isobutylene | Downflow | A | 100 | 500 | 22 | 100 | 37 | 51 | 12 | — |
| Isobutylene | Upflow | A | 100 | 500 | 22 | 100 | 17 | 56 | 24 | 4 |
| 1-butene | Downflow | A | 150 | 500 | 7 | 93[a] | 51 | 34 | 15 | — |
| 1-butene | Upflow | A | 150 | 500 | 7 | 95[b] | 38 | 31 | 19 | 12 |
| Propylene | Upflow | B | 150 | 500 | 5 | 50 | [c] | | | |

[a] 93% conversion of 1-butene. Selectivity to $C_4$ oligomers was 85%. Remaining 15% selectivity was to 2-butene.
[b] 95% conversion of 1-butene. Selectivity to $C_4$ oligomers was 87%. Remaining 13% selectivity was to 2-butene.
[c] Selectivities (%) to $C_6^=$, $C_9^=$, $C_{12}^=$, $C_{15}^=$+ were about 25, 55, 15 and 5, respectively.

The liquid obtained from the downflow reaction of the isobutylene at 100° C. described above was examined as a blending agent for gasoline. This is compared to toluene as a blending agent. The results are shown in Table II. The isobutylene oligomers provide as good a blending agent as toluene.

TABLE II

BLENDING OCTANE NUMBERS FOR LIQUIDS OBTAINED FROM ISOBUTYLENE OLIGOMERIZATION. - COMPARISON TO TOLUENE[a]

| BLENDING AGENT | BRON[b] | BMON[c] | B(R + M)/2[d] |
|---|---|---|---|
| Isobutylene Oligomer | 116.2 | 91.0 | 103.6 |
| Toluene | 113.8 | 91.7 | 102.8 |

[a]Run as 10% v blends in Shell 25922, a regular unleaded gasoline (RON = 91.2, MON = 83.0, R + M/2 = 87.1).
[b]Blending research octane number.
[c]Blending motor octane number.
[d]Blending research plus blending motor octane numbers averaged.

A mixed hexene stream was fed to the reactor in a downflow mode. The reaction conditions were 100° C., 100 psi and a LHSV of 10 hr$^{-1}$. Upon reaction, conversion of $C_6$ was 59%; selectivity to $C_{12}$ was 69%, to $C_{18}$ was 14% and to $C_{24}{}^+$ was 17%. Analysis of the hexenes in the feed and product stream is shown in Table III. The results shown that olefins substituted on the olefinic carbon atoms (entries 4, 5, 9 and 10) react much more readily than olefins not so substituted (entries 1, 2, 3, 7 and 8). These isobutylene-type olefins (4, 5, 9 and 10) are greatly reduced in the product stream due to oligomerization to higher products. The remaining olefins increase due to the selective oligomerization of the isobutylene type olefins.

TABLE III

OLIGOMERIZATION OF A HEXENE STREAM FROM A PROPYLENE FED DIMERSOL UNIT

| OLEFIN | COMPOSITION (%), BEFORE | COMPOSITION (%), AFTER |
|---|---|---|
| 1 1-Hexene | 0.4 | 0.5 |
| 2 2-Hexene | 17.2 | 23.0 |
| 3 3-Hexene | 5.3 | 8.5 |
| 4 2-Methyl-1-pentene | 5.4 | 2.0 |
| 5 2-Methyl-2-pentene | 39.2 | 8.5 |
| 6 3-Methyl-2-pentene | — | 1.0 |
| 7 4-Methyl-2-pentene | 22.8 | 49.5 |
| 8 4-Methyl-1-pentene | 1.0 | 2.5 |
| 9 2,3-Dimethyl-1-butene | 1.9 | 1.0 |
| 10 2,3-Dimethyl-2-butene | 5.3 | 2.5 |
| 11 Unknown | 1.5 | 1.0 |

I claim:

1. A process for oligomerizing olefins of the following general formula $R^1R^2C=CR^3R^4$ where $R^1$, $R^2$ and $R^3$ are individually hydrogen or alkyl of 1 to about 20 carbon atoms and $R^4$ is alkyl of 1 to about 20 carbon atoms, unless all of $R^1$, $R^2$ and $R^3$ are hydrogen, then $R^4$ is alkyl of 1 to about 6, with the proviso that any two of the Rs may form a divalent alkylene moiety of 2 to about 20 carbon atoms, to higher olefinic oligomers which process comprises contacting said olefins at a temperature of from about 10° C. to about 350° C. with a catalyst which comprises pentavalent tantalum, halogen, oxygen and a metal oxide substrate wherein at least one valence of tantalum is bound to oxygen which is bound to the substrate, at least one valence at the tantalum is bound to halogen and the remaining tantalum valences are bound to halogen and/or oxygen which may or may not be bound to the substrate.

2. The process of claim 1 wherein said substrate is silica, alumina, silica-alumina, zeolite, open lattice clay or mixtures thereof and the halogen is chloride or fluoride or mixtures thereof.

3. The process of claim 1 wherein said substrate has a major component of silica or alumina or a mixture thereof and the halogen is chloride or fluoride or a mixture thereof.

4. The process of claim 1 wherein the pressure ranges from about atmospheric to about 5000 psi.

5. The process of claim 1 wherein the pressure ranges from about atmospheric to about 2000 psi.

6. The process of claim 1 wherein the temperature ranges from about 50° C. to about 250° C.

7. Process of claim 1 wherein $R^1$, $R^2$ and $R^3$ are individually hydrogen or alkyl of 1 to about 10 carbon atoms and $R^4$ is alkyl of 1 to about 10 carbon atom unless all of $R^1$, $R^2$ and $R^3$ are hydrogen then $R^4$ is alkyl of 1 to about 4 carbon atoms.

8. The process of claim 1 wherein the catalyst is prepared by a process which comprises subliming tantalum pentahalide(s) and reacting in a substantially anhydrous and oxygen-free atmosphere vapor therefrom with a substantially anhydrous, hydroxyl-containing metal oxide substrate.

9. The process of claim 1 wherein the catalyst is prepared by a process which comprises:
(a) subliming tantalum pentachloride and reacting in a substantially anhydrous and oxygen-free atmosphere vapor therefrom with a substantially anhydrous, hydroxyl-containing metal oxide substrate,
(b) contacting the product of step (a) with an oxygen-containing atmosphere and
(c) contacting the product of step (b) with a liquid or gaseous fluorinated hydrocarbon.

* * * * *